United States Patent [19]
Sand

[11] Patent Number: 5,304,169
[45] Date of Patent: Apr. 19, 1994

[54] METHOD FOR COLLAGEN SHRINKAGE

[75] Inventor: Bruce J. Sand, Hidden Hills, Calif.

[73] Assignee: Laser Biotech, Inc., Los Angeles, Calif.

[21] Appl. No.: 930,973

[22] Filed: Aug. 17, 1992

Related U.S. Application Data

[63] Continuation of Ser. No. 771,547, Oct. 4, 1991, abandoned, which is a continuation-in-part of Ser. No. 546,252, Jun. 29, 1990, Pat. No. 5,137,530, which is a continuation-in-part of Ser. No. 374,958, Jun. 30, 1989, Pat. No. 4,976,709, which is a continuation-in-part of Ser. No. 285,379, Dec. 15, 1988, abandoned, which is a continuation of Ser. No. 170,070, Mar. 14, 1988, abandoned, and a continuation of Ser. No. 67,381, Jun. 24, 1987, abandoned, and a continuation of Ser. No. 914,169, Oct. 1, 1986, abandoned, which is a continuation-in-part of Ser. No. 781,225, Sep. 27, 1985, abandoned.

[51] Int. Cl.⁵ ............................................. A61B 17/32
[52] U.S. Cl. ..................................................... 606/5
[58] Field of Search ................................. 606/3–5, 606/13–16; 128/395–398

[56] References Cited

U.S. PATENT DOCUMENTS

| | | | |
|---|---|---|---|
| 3,776,230 | 12/1973 | Neefe . | |
| 4,461,294 | 7/1984 | Brown | 606/5 |
| 4,538,608 | 9/1985 | L'Esperance | 606/3 |
| 4,665,913 | 5/1987 | L'Esperance | 606/3 |
| 4,669,466 | 6/1987 | L'Esperance | 606/3 |
| 4,976,709 | 12/1990 | Sand | 606/5 |

FOREIGN PATENT DOCUMENTS

| | | | |
|---|---|---|---|
| 0402250 | 12/1990 | European Pat. Off. . | |
| 3148748 | 7/1983 | Fed. Rep. of Germany | 606/4 |
| 9012618 | 4/1990 | PCT Int'l Appl. . | |

OTHER PUBLICATIONS

Mainster, "Opthalmic applications of infrared lasers--thermal considerations" Assoc. for Res. in Vis. & Ophth. Apr. 1979.

Cotliar et al., "Examer Laser Radical Keratomy", Opthalmology Feb. 1985.

Jackson, D. S. "The Nature of Collagen-Chondroitin Sulphate Linkages in Tendon", *Rheumatism Research Center, University of Manchester*, vol. 56, pp. 699–703, (Oct. 12, 1953).

Jackson, D. S. "Chrondroitin Sulphuric Acid as a Factor in the Stability of Tendon", *Rheumatism Research Center, University of Manchester*, vol. 54, pp. 638–641, (Jan. 9, 1953).

Seiler, et al., "Laser Thermokeratoplasty by Means of a Pulsed Holmium: YAG Laser for Hyperopic Correction", *Refractive & Corneal Surgery*, vol. 6, pp. 335–339, (Sep./Oct. 1990).

Horn et al., "New refractive method for laser thermal keratoplasty with the Co:MgF$_2$ laser", *J. Cataract Refract Surg.*, vol. 16, pp. 611–616, (Sep. 16, 1990).

Spears et al., "Corneal refractive correction by laser thermal keratoplasty", *SPIE*, vol. 1202 Laser-Tissue Interaction (1990).

*Primary Examiner*—Max Hindenburg
*Attorney, Agent, or Firm*—Majestic, Parsons, Siebert & Hsue

[57] ### ABSTRACT

A method for shrinkage of collagen tissue by application of coherent infrared energy, in which the threshold shrinkage temperature is substantially reduced by application of a reagent such as lysozyme to the tissue prior to heating. The method is especially useful in ophthalmology for shape modification of a cornea, and is enhanced by using a corneal collagen shield as a carrier and delivery agent for the reagent and an admixed anaesthetic.

37 Claims, No Drawings

METHOD FOR COLLAGEN SHRINKAGE

CROSS-REFERENCE TO RELATED APPLICATIONS

This is a continuation of application Ser. No. 07/771,547, filed Oct. 4, 1991, now abandoned, which is a continuation-in-part of application Ser. No. 07/546,252 (Jun. 29, 1990) and now U.S. Pat. No. 5,137,530 which is a continuation-in-part of application Ser. No. 07/374,958 (Jun. 30, 1989 and now U.S. Pat. No. 4,976,709) which is a continuation-in-part of application Ser. No. 07/285,379 (Dec. 15, 1988) abandoned which is a continuation of applications Ser. Nos. 07/170,070 (Mar. 14, 1988) abandoned 07/067,381 (Jun. 24, 1987) abandoned, and 06/914,169 (Oct. 1, 1986) abandoned, the latter being a continuation-in-part of application Ser. No. 06/781,225 (Sep. 27, 1985), abandoned.

BACKGROUND OF THE INVENTION

My U.S. patent application Ser. No. 07/546,252 and U.S. Pat. No. 4,976,709, the entire disclosures of which are incorporated herein by reference, describe methods and apparatus for achieving controlled shrinkage of collagen tissue. These prior inventions have application to collagen shrinkage in many parts of the body, and are particularly useful in an ophthalmological procedure for achieving controlled shape changes in the cornea of the eye for correction of refractive errors.

As described in detail in the application and patent which are incorporated by reference, a presently preferred collagen-shrinkage technique involves use of laser coherent energy in a wavelength range of about 1.80 to about 2.55 microns, or of such coherent infrared energy of wavelengths corresponding to collagen absorption coefficients in the range of about 15 to 120 $cm^{-1}$. Irradiation of collagen with such energy is controlled to elevate the collagen temperature to at least 23° C. above normal body temperature to achieve collagen shrinkage.

As explained in my referenced prior disclosures, a critical factor in shrinkage of corneal collagen of the eye is avoidance of excessive tissue-destructive temperature increases throughout the corneal stroma, and especially in the outer epithelial and inner endothelial layers of the cornea. A lowering of the threshold temperature at which collagen shrinkage occurs will provide an added measure of safety in avoiding tissue-destructive temperature increases, and it is to this goal that the present invention is directed.

SUMMARY OF THE INVENTION

This invention relates to a process for collagen shrinkage by application of coherent infrared energy, preceded by application of a reagent to the collagen tissue for reduction of the shrinkage threshold temperature. Presently preferred reagents include hyaluronidase, and (especially) lysozyme. The resulting threshold-temperature reduction of about 10° C. to 12° C. enables use of lower energy levels. The infrared energy is preferably supplied by a laser operating in the wavelength range of about 1.8 to about 2.55 microns.

The invention is described with specific reference to ophthalmic applications in which a corneal shape change is effected to correct refractive errors of the eye. In this application, the reagent is mixed with an anaesthetic, and the mixture is impregnated in a contact-lens-like corneal collagen shield which is then applied to the cornea. After the mixture is absorbed by the cornea, the laser energy is applied, preferably repetitively in different corneal zones, to heat the corneal stroma, and thereby to cause the desired shrinkage and shape change.

DESCRIPTION OF THE PREFERRED EMBODIMENT

Interstitial collagen (Type I) consists of a continuous triple helical molecule which is 300 nanometers in length. The parent molecule is procollagen. The triple helix is formed by three polypeptide chains. Each chain forms a left-handed polyproline II helix which interacts with two other helices to form a right-handed superhelix.

Mammalian collagen is generally considered to be stabilized by electrovalencies located at polar side chains to form salt-like cross-linkages, and coordinate valencies between adjacent peptide groups (hydrogen bonds). Destabilization of collagen will result from removal of an amorphous substance (Glycosaminoglycan or GAG which includes chondroitin sulfuric acid or CSA) which cements collagen fibers together into fiber bundles. Destabilization also results from cleaving the intermolecular hydrogen bonds to cause a helix-to-coil transition.

Anything which interferes with the interaction of any interchain linkage will inevitably influence the thermal transformation temperature. Shrinkage temperature may be defined as the specific point at which disruptive tendencies exceed the cohesive forces, thus making this temperature an actual measurement of the structural stability of collagen expressed in thermal units.

Normal stabilized collagen fibers are stable up to a temperature of 58° C. to 60° C., and shrinkage occurs within a small temperature range between about 60° C. and 70° C. Major conformational changes occur in the molecule before unfolding, however. Predenaturational transition is observed by calorimetric measurements, and the molecule contains micro-unfolded states at temperatures below the melting temperature.

An increase in upper-limit thermal stability ($T_2$) of collagen fibers with age is interpreted as resulting from an increased number of hydrogen bonds in progressive cross-linkage of the collagen structure. This is related to progressive sclerosis. Normal tendon collagen has a shrinkage temperature threshold which is 2° C. to 4° C. less than the corresponding threshold for skin collagen.

Ultrastructural changes take place far below the point of thermal shrinkage, but collagen fibers kept for a protracted period at elevated temperatures considerably below their $T_s$ show beginning shrinkage as shown by topo-optical staining reactions and polarization optical analysis. This indicates a gradual and continuous change of the micellar texture of the collagen during the earliest stages of thermal shrinkage.

Transmission polarizing microscopy enables high-resolution observation of morphological changes and characteristics not seen with routine light microscopy. Tissue birefringence is detected by illuminating microscopic tissue section with incident light polarized 90 degrees to an optical analyzer located above the section creating a dark field.

These techniques of evaluating the gradual diminution of intensity and the color change in collagen birefringence caused by thermal alteration provide a succession of tissue damage markers and temperature ranges between the onset of collagen ultrastructural changes, helix-to-coil transition, and denaturation. Knowledge of the thermal damage coefficients for birefringent changes has been indispensable in the development of dosimetry models for the application of collagen shrinkage by means of the present method.

While these methods are disclosed for evaluating collagen shrinkage in general, special reference is made for their application to corneal stroma for the purpose of refractive modification. For safe and efficacious collagen shrinkage to result in a therapeutic benefit such as refractive modification of corneal curvature, shrinkage must occur well below the thermal damage threshold. As the damage threshold is exceeded, two orders of destruction occurs.

The first order of damage results in collagen (protein) denaturation which, in turn, provides the stimulus for the inflammatory response resulting in removal of damaged tissue by the multipotential keratocyte. Subsequent fibrillogenesis yields new collagen fibrils of pretreatment dimensions, and undesired early regression of the desired refractive result. The second order of damage results in permanent pathology with folds in Descemet's membrane and endothelial destruction.

The present invention is an adjunctive process to laser-induced collagen thermal shrinkage for the purpose of increasing the margin of safety between the thermal shrinkage temperature and the thermal damage temperature.

The pretreatment of collagen connective tissue with an chemical or reagent which acts upon the CSA and/or the hydrogen bonding of the fibrils will reduce the thermal stability ($T_s$) and thus the thermal shrinkage temperature of the collagen. Examples of such chemicals are hyaluronidase, lysozyme and beta-naphthalenesulfuric acid which degrade the CSA by eliminating the salt-like cross-linkages alone. This will reduce shrinkage temperature by 10°-12° C.

Urea, calcium chloride solution and periodic acid all break hydrogen bonds, and can, in concentrated form, excessively lower the threshold temperature by as much as 40° C. This of course means that hydrogen bond formation is the more important in determining fiber stability. Solutions of the reagents are believed to be useful in achieving a more modest reduction of shrinkage temperature by perhaps 10° to 15° C.

An effective way of titrating the reduction of thermal shrinkage temperature during laser thermal keratoplasty involves use of a corneal collagen shield which is an ophthalmological product available from companies such as Chiron and Bausch & Lomb. Soaking a shield of this type in a mixture of topical anesthetic such as tetracaine and the desired $T_s$ reducing reagent of the appropriate concentration has several distinct advantages. The anesthetic mixture assists in the penetration of the threshold-reducing reagent through the corneal epithelium which is a mechanical barrier for the chemical. At the same time, the cornea is anesthetized in preparation for the laser thermal keratoplasty procedure.

The use of lysozyme to reduce the cement substance of the corneal collagenous stroma has several distinct advantages over similar reacting reagents. Lysozyme is a naturally occurring protein in lacrimal secretion, and is well tolerated by the ocular epithelial surfaces. Lysozyme is a relatively small molecule (molecular weight of about 14,000, as compared to hyaluronidase of about five times greater weight) which more readily penetrates the epithelium in an anaesthetic vehicle. A more efficacious equilibrium of concentration is thereby maintained within the CSA of the corneal stroma.

The collagen shield resembles a translucent contact lens, and is fabricated from bovine or porcine collagen tissue which resembles the collagen molecule of the human eye, but it is not cross-linked. The shield promotes epithelial healing, and protects the cornea after coherent energy exposure. It lubricates and provides a heat sink during the exposure procedure, and biodegrades within approximately 12 hours.

The sustained release of the $T_s$ reducing chemical (such as urea or lysozyme) acts to gradually sensitize the stromal collagen to a reduced thermal shrinkage temperature, providing the desired thermal margin of safety, and assuring collagen shrinkage and refractive modification without the attendant damage risk of other methods.

In use, the collagen shield is placed in a shallow plastic cup (supplied by the shield manufacturer), and is irrigated with and completely immersed in about five milliliters of an ophthalmic topical anaesthetic such as tetracaine or proparacaine. About five droplets of the desired threshold-temperature reducing reagent (e.g., lysozyme) are added to the cup to provide a concentration of about 10 percent in the anaesthetic vehicle. The shield remains immersed in the anaesthetic and reagent mixture for about five minutes to assure complete absorption by the shield.

The liquid-loaded and lubricated collagen shield is then inserted against the eye surface in the same fashion used to install a soft contact lens. The patient's eyelids are closed over the shield for about five minutes to enable corneal absorption of the anaesthetic and reagent. The patient is forewarned of a probable transient discomfort as the anaesthetic is released into the lacrimal layer of the eye. After the corneal-absorption period has elapsed, the patient is positioned against the usual chin and forehead rests of a biomicroscope, and the shrinkage-producing laser exposure treatment proceeds.

The collagen shield provides a number of advantages in the overall treatment program. It provides a "sustained release" vehicle for the reagent, and maintains proper concentration within the lacrimal layer. The same sustained-release action maintains protracted anaesthesia (for several hours beyond that resulting from conventional topical application) for patient comfort after laser exposure.

The shield also lubricates the cornea during prolonged laser exposure (the blink reflex being inhibited by the anaesthetic), and promotes epithelial regeneration if cell damage occurs from prolonged anaesthetic exposure. Importantly, the shield further provides a heat sink at the corneal surface to minimize epithelial temperature elevation during laser exposure, and to maintain a desired peak-temperature profile in the anterior midstroma of the cornea as discussed in the disclosures incorporated herein by reference. The shield biodegrades after about twelve hours, and acts in much the same manner as a bandage lens during that period.

While laser exposure parameters (energy levels and duration) are adjusted to allow for energy absorption by the corneal shield, the overall result is that lower energy levels are delivered to the corneal stroma to cause the desired shrinkage. Using the reagents already described, threshold temperature is reduced to about 48°

C. which is only 11° C. above body temperature, and well below the temperature at which collagen denaturation or endothelial damage is likely.

Though not fully evaluated, it is expected that laser exposure parameters (using a THC:YAG laser at 2.08 microns) will involve pulsed energy application at one to three pulses per second, with a pulse width of one to eight milliseconds, and at an energy level of about 25 millijoules.

The post-treatment of mammalian collagen, that is the use of an agent after laser exposure, will also result in enhancement of the shrinkage effect and thus increase refractive alteration. Beta-aminoproprionitrile is such an agent and will inhibit cross-linking mediated by the copper-dependent enzyme lysyl-oxidase by preventing disulphide bonds from developing.

The judicious and appropriate use of the herein disclosed methods in association with laser thermal keratoplasty as described in my referenced disclosures will yield predictable and efficacious refractive changes without undesirable damage to adjacent corneal tissue, and without the subsequent regression of refractive alteration and permanent corneal pathology.

While the invention has been described primarily in terms of corneal refractive modification, the disclosed procedure, modified appropriately for the characteristics of the target collagen tissue, will be efficacious for collagen modification throughout the body.

What is claimed is:

1. A method for shrinking collagen tissue, comprising the application of a reagent to the tissue to reduce threshold shrinkage temperature, followed by irradiation of the tissue with energy having a wavelength in the range of about 1.80 to about 2.55 microns.

2. The method of claim 1 in which the reagent is lysozyme.

3. The method of claim 1 in which the reagent is selected from a group consisting of hyaluronidase and beta-naphthalene-sulphuric acid.

4. The method of claim 1 in which the reagent is selected from a group consisting of solutions of urea, calcium chloride and periodic acid.

5. The method of claim 1 in which the reagent is selected to produce a lowering of the threshold temperature at which shrinkage occurs by at least about 10° C.

6. The method as defined in claims 1, 2, 3, 4 or 5, in which the collagen tissue is corneal collagen tissue.

7. The method as defined in any one of the claims 1-5 in which the energy is supplied by a laser.

8. The method as defined in any one of the claims 1-5 in which the energy is supplied by a laser and the collagen tissue is corneal collagen tissue.

9. The method as defined in any one of the claims 1-5 wherein the irradiation is caused to raise the temperature of the collagen tissue sufficient to cause the tissue to shrink but not so high as to cause any substantial damage to the tissue.

10. The method as defined in any one of claims 1-5 wherein the irradiation is caused to raise the temperature of the collagen tissue sufficient to cause the tissue to shrink but not so high as to cause any substantial damage to the tissue and the energy is supplied by a laser.

11. The method as defined in any one of the claims 1-5 wherein the irradiation is caused to raise the temperature of the collagen tissue sufficient to cause the tissue to shrink but not so high as to cause any substantial damage to the tissue and the collagen tissue is corneal collagen tissue.

12. The method as defined in any one of claims 1-5 wherein the irradiation is caused to raise the temperature of the collagen tissue sufficient to cause the tissue to shrink but not so high as to cause any substantial damage to the tissue, the energy is supplied by a laser, and the collagen tissue is corneal collagen tissue.

13. A keratoplasty method for shape modification of a cornea, comprising the application of a reagent to stromal collagen tissue of the cornea to reduce the threshold shrinkage temperature of the tissue to a range substantially above body temperature and below about 60° C., followed by irradiation of the tissue with energy of infrared wavelength corresponding to corneal-collagen absorption coefficients in the range of about 15 to about 120 cm$^{-1}$, thereby heating and shrinking the tissue.

14. The method of claim 13 in which the reagent is lysozyme.

15. The method of claim 13 in which the reagent is selected from a group consisting of hyaluronidase and beta-naphthalene-sulphuric acid.

16. The method of claim 13 in which the reagent is selected from a group consisting of solutions of urea, calcium chloride and periodic acid.

17. The method of claim 13 in which the reagent is selected to produce a lowering of the threshold temperature at which shrinkage occurs by at least about 10° C.

18. The method as defined in any one of claims 13-17 in which the energy is supplied by a laser.

19. The method as defined in any one of claims 13-17 wherein the irradiation is caused to raise the temperature of the corneal collagen tissue sufficient to cause the corneal tissue to shrink but not so high as to cause any substantial damage to any of the corneal tissue, an outer epithelial corneal layer or an inner endothelial corneal layer.

20. The method as defined in any one of claims 13-17 wherein the irradiation is caused to raise the temperature of the corneal collagen tissue sufficient to cause the corneal tissue to shrink but not so high as to cause any substantial damage to any of the corneal tissue, an outer epithelial corneal layer or an inner endothelial corneal layer, and the energy is supplied by a laser.

21. A keratoplasty method for shape modification of a cornea, comprising the steps of selecting a reagent which is effective in reducing a threshold shrinkage temperature of collagen tissue of the cornea, impregnating a corneal collagen shield with the reagent, applying the shield to the cornea to dispense the reagent into the corneal collagen tissue, and irradiating the cornea with energy having a wavelength in the range of 1.80 to 2.55 microns to effect heating and shrinkage and portions of the corneal collagen tissue.

22. The method of claim 21, and further comprising the step of mixing the reagent with an ophthalmic anaesthetic before the step of impregnating the shield.

23. The method of claim 22 in which the energy is supplied by a laser.

24. The method of claim 23 in which the energy is applied to the cornea in repetitive pulses.

25. The method of claim 24 in which the energy is applied to spaced-apart zones in the cornea to effect an overall corneal shape change with corrects a refractive error.

26. The method of claim 25 in which the reagent is lysozyme.

27. The method of claim 25 in which the reagent is selected from a group consisting of hyaluronidase and beta-naphthalene-sulphuric acid.

28. The method of claim 25 in which the reagent is selected from a group consisting of solutions of urea, calcium chloride and periodic acid.

29. The method of claim 25 in which the anaesthetic is selected from a group consisting of tetracaine and proparacaine.

30. The method of claim 25 in which the step of irradiating and shrinking the collagen tissue is followed by application of beta-aminoproprionitrile to the tissue.

31. The method as defined in any one of claims 21-30 wherein the irradiation is caused to raise the temperature of the corneal collagen tissue sufficient to cause the corneal tissue to shrink but not so high as to cause any substantial damage to any of the corneal tissue, an outer epithelial corneal layer or an inner endothelial corneal layer.

32. A method of reshaping the curvature of a cornea, comprising the steps of:

applying to collagen tissue within the cornea a reagent that causes a threshold temperature above which the collagen tissue will shrink to be reduced from a normal threshold shrinkage temperature that exists without use of the reagent, providing a source of energy within a wavelength range of about 1.80 to about 2.55 microns, exposing the collagen tissue to said energy in a manner to raise the temperature thereof sufficient to cause the collagen tissue to shrink while maintaining its temperature below said normal threshold shrinkage temperature, thereby to cause the curvature of the cornea to be reshaped.

33. The method according to claim 32 in which the reagent is lysozyme.

34. The method according to claim 32 in which the reagent is selected from a group consisting of hyaluronidase and beta-naphthalene-sulfuric acid.

35. The method according to claim 32 in which the reagent is selected from a group consisting of solutions of urea, calcium chloride and periodic acid.

36. The method according to claim 32 in which the reagent is selected to produce a lowering of the threshold temperature at which shrinkage occurs by at least about 10° C.

37. The method as defined in any one of claims 32-36 wherein the energy source providing step includes the step of providing a laser that generates coherent infrared energy.

* * * * *

UNITED STATES PATENT AND TRADEMARK OFFICE
CERTIFICATE OF CORRECTION

PATENT NO. : 5,304,169
DATED : April 19, 1994
INVENTOR(S) : Bruce J. Sand

It is certified that error appears in the above-indentified patent and that said Letters Patent is hereby corrected as shown below:

In Column 6, Claim 25, line 65:  change "with" to --which--

Signed and Sealed this

Thirteenth Day of September, 1994

Attest:

BRUCE LEHMAN

Attesting Officer    Commissioner of Patents and Trademarks